(12) United States Patent
Yamaya et al.

(10) Patent No.: US 8,222,608 B2
(45) Date of Patent: Jul. 17, 2012

(54) PET SCANNER AND METHOD FOR DECIDING ARRANGEMENT OF DETECTORS

(75) Inventors: Taiga Yamaya, Chiba (JP); Hideo Murayama, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 0 days.

(21) Appl. No.: 12/936,464

(22) PCT Filed: Apr. 14, 2008

(86) PCT No.: PCT/JP2008/057284
§ 371 (c)(1),
(2), (4) Date: Oct. 5, 2010

(87) PCT Pub. No.: WO2009/128131
PCT Pub. Date: Oct. 22, 2009

(65) Prior Publication Data
US 2011/0024638 A1 Feb. 3, 2011

(51) Int. Cl.
*G01T 1/166* (2006.01)
(52) U.S. Cl. .................................. 250/363.05
(58) Field of Classification Search .. 250/363.01–363.1, 250/370.01–370.15; 378/98.8
See application file for complete search history.

(56) References Cited

U.S. PATENT DOCUMENTS

2007/0018108 A1* 1/2007 Kitamura ................. 250/363.02

FOREIGN PATENT DOCUMENTS

JP A-9-211130 8/1997
JP A-2001-141827 5/2001

OTHER PUBLICATIONS

Yamaya at al., "A proposal of an open PET geometry," Physics in Medicine and Biology, 2008, pp. 757-773, vol. 53.
Yamaya et al., "Imaging Simulation of Open PET Geometries," The Institute of Electronics, Information and Communication Engineers Technical Report, Jan. 18, 2008, pp. 383-387, vol. 107—No. 461 (with Abstract).
International Search Report mailed Jun. 24, 2008 issued in International Patent Application No. PCT/JP2008/057284 (with translation).

* cited by examiner

*Primary Examiner* — Kiho Kim
(74) *Attorney, Agent, or Firm* — Oliff & Berridge, PLC

(57) ABSTRACT

A PET scanner in which detector rings are arrayed in a multilayered manner so as to oppose each other in the body axis direction is provided. In the PET scanner, a predetermined number of detector units, each of which is made up of a predetermined number of detector rings, are arrayed so as to give each other a clearance, and a first ring set in which the clearance is less than or equal to a mean value of widths of two detector units forming each clearance and a second ring set constituted with a predetermined number of detector units are arrayed apart so as to give a clearance which is less than or equal to a mean value of the width of the first ring set and that of the second ring set, thereby imaging a field-of-view including the clearance and continuing in the body axis direction to an entire length of the first ring set and that of the second ring set.

10 Claims, 19 Drawing Sheets

Fig. 11
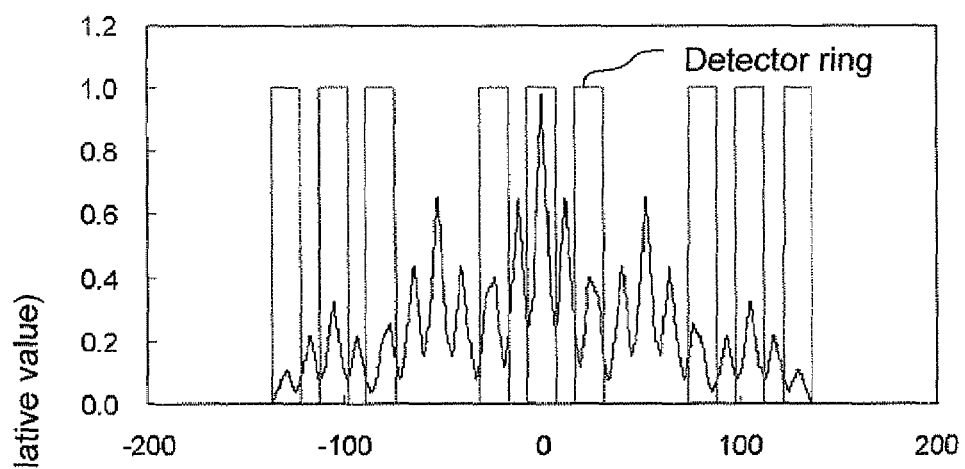
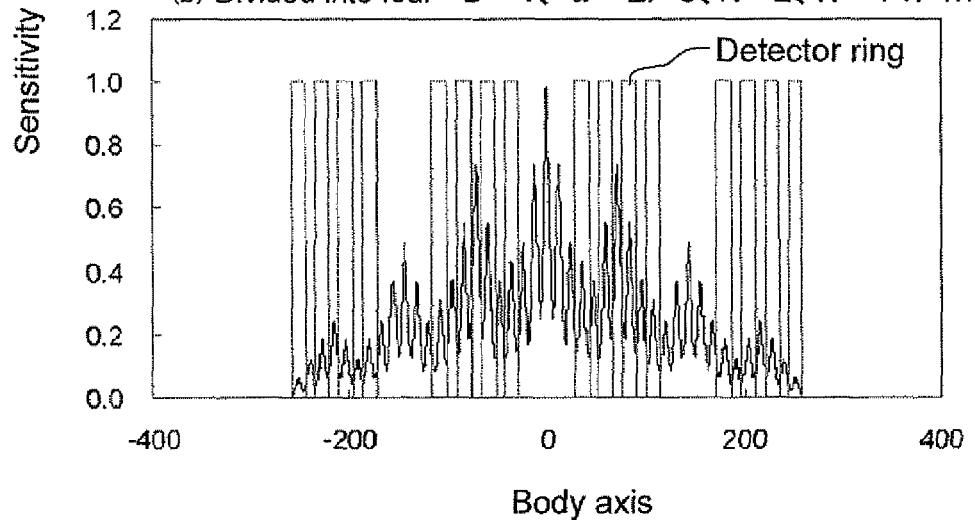
Body axis

* In drawing, numeral indicates size of gap (numeral in parentheses indicates number of corresponding rings).

Fig. 15
(a) Before multilayered Arrangement (open region width G0 = 150 mm)
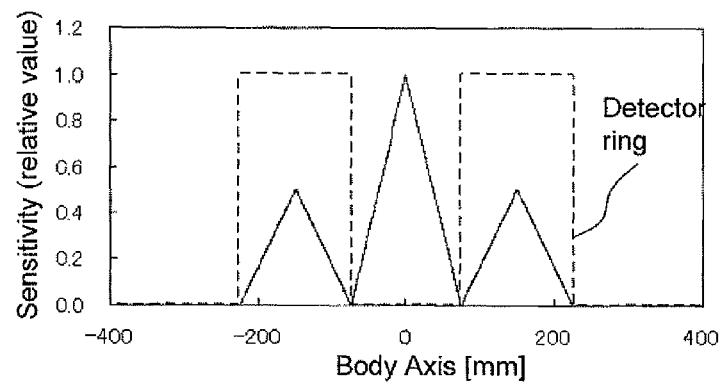
(b) Result of optimization under conditions of G0 = 150 mm and Weva = 150mm
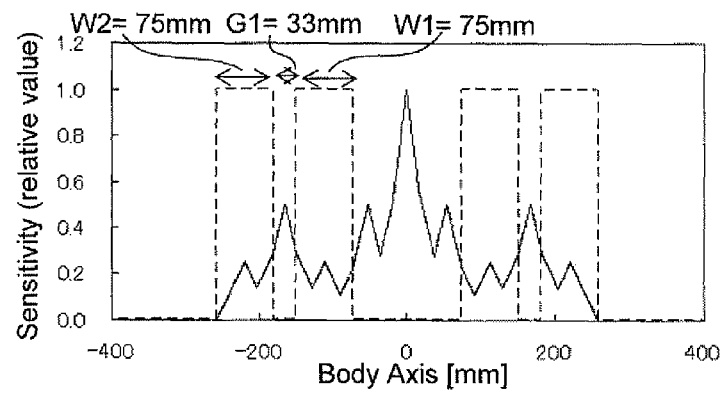
(c) Result of optimization under conditions of G0 = 200 mm and Weva = 500mm
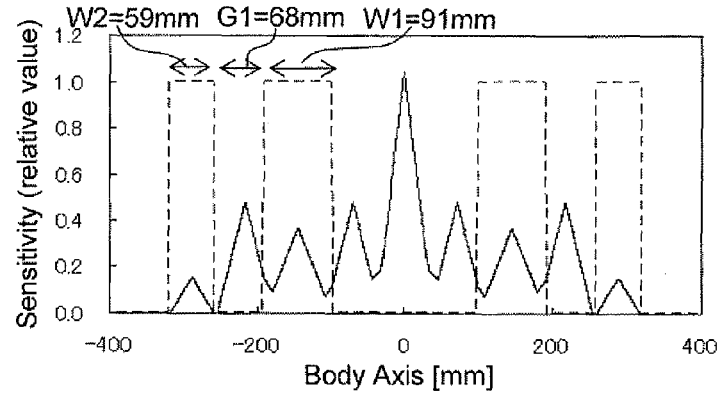

PET SCANNER AND METHOD FOR DECIDING ARRANGEMENT OF DETECTORS

TECHNICAL FIELD

The present invention relates to a PET scanner in which detector rings are arrayed in a multilayered manner so as to oppose each other in the body axis direction and a predetermined number of detector units, each of which is made up of a predetermined number of detector rings, are arrayed so as to give each other a clearance, thereby imaging a continuous field-of-view including the clearance in the body axis direction and also to a method for deciding an arrangement of detectors. The present invention relates in particular to a PET scanner capable of enlarging a clearance and a field-of-view in the body axis direction without increasing the number of detectors and also to a method for deciding an arrangement of the detectors therefore.

BACKGROUND ART

Positron emission tomography (PET) has gained attention as being effective in making an early diagnosis of cancers, cerebrovascular disorders, dementia and others. PET is a method for injecting a compound labeled with a trace amount of a positron emission nuclide to detect annihilation radiation emitted from the body, thereby imaging of metabolic functions such as sugar metabolism and examining the presence or absence of a disease and the seriousness of a disease. For the implementation thereof, PET scanners have been put into practical use.

The principle of PET is as follows. Positrons emitted from a positron emission nuclide by positron decay undergo pair annihilation with electrons in the vicinity, and the thus generated pair annihilation radiation at 511 keV is determined by a pair of radiation detectors according to the principle of coincidence. Thereby, the position at which the nuclide is present can be localized on one line segment (coincidence line) connecting between the pair of detectors. When an axis from the head of a patient to the feet is defined as a body axis, a distribution of the nuclide on a planar surface intersecting perpendicular with the body axis is obtained by image reconstruction in two-dimensional mode from data of the coincidence line determined on the planar surface in various directions.

Therefore, earlier PET scanners were constituted with single ring-type detectors in which detectors were arranged on a planar surface which was given as a field-of-view densely in a ring shape so as to surround the field-of-view. Thereafter, with the advent of a multiple ring-type detector in which many single ring-type detectors were densely arranged in the body axis direction, a field-of-view in two-dimensional mode was changed to that in three-dimensional mode. Further, in the 1990s, the coincidence was also determined between the detector rings to develop 3-D mode PET scanners one after another with a great increase in sensitivity. This trend is found even now.

In order to increase the sensitivity of a PET scanner, as illustrated in FIG. 1($a$), it is necessary that detectors are arranged densely in a tunnel shape to constitute a multiple ring-type detector 10, thereby increasing a solid angle. However, a long tunnel-shaped patient port not only causes increased psychological stress to a patient 6 under examination but also affects medical care of the patient. In order to cope with this problem, as illustrated in FIG. 1($b$), the applicant has proposed an open-type PET scanner in which multiple ring-type detectors 11, 12 which have been divided into plural regions in the body axis direction of a patient 6 are arranged apart to have a field-of-view region (also referred to as an open field-of-view) which is physically opened. In an open region, as shown in FIG. 2, an image is reconstructed from remaining coincidence lines between the multiple ring-type detectors 11, 12. In this drawing, the numeral 8 depicts a bed.

Here, as shown in FIG. 3, when a dimension (also referred to as a width) of each of the multiple ring-type detectors 11, 12 in the body axis direction is given as W and a dimension of the open region in the body axis direction (also referred to as a clearance) exceeds W, a region which can be imaged is discontinued in the body axis direction. Therefore, as shown in FIG. 3($a$), a maximum value of an open-region clearance for obtaining a field-of-view continuing in the body axis direction is given as W. In this instance, a whole field-of-view in the body axis direction is given as 3W. However, a drastic reduction in sensitivity is caused at both ends of the open region.

Therefore, as shown in FIG. 3($b$), the open-region clearance is given as $\alpha$W ($0<\alpha\leq 1$) to overlap the sensitivity, thus making it possible to prevent a reduction in sensitivity at both ends of the open region. In this instance, a field-of-view in the body axis direction is given as $(2+\alpha)$W. As $\alpha$ is made smaller, the reduction in local sensitivity is suppressed accordingly, while the open-region clearance and the field-of-view in the body axis direction are reduced (refer to Taiga Yamaya, Taku Inaniwa, Shinichi Minohara, Eiji Yoshida, Naoko Inadama, Fumihiko Nishikido, Kengo Shibuya, Chih Fung Lam and Hideo Murayama, "A proposal of an open PET geometry," Phy. Med. Biol., 53, pp. 757-773, 2008.).

In the open-type PET scanner previously proposed by the applicant, maximum values of an open-region clearance and a field-of-view in the body axis direction are respectively limited to W and 3W. Therefore, in order to further enlarge the open-region clearance and the field-of-view in the body axis direction, it is necessary to enlarge W itself. However, there is a problem that an increase in the number of detectors constituting one multiple ring-type detector makes the scanner more expensive and complicated.

DISCLOSURE OF THE INVENTION

The present invention has been made to solve the above-described conventional problem, an object of which is to enlarge an open-region clearance and a field-of-view in the body axis direction, without increasing the number of detectors.

In the present invention, a plurality of detector rings, each of which is constituted with detecting elements or detecting element blocks equal or different in width are arranged in the body axis direction, thereby securing a long field-of-view from the detector at one end to that at the other end when viewed in the body axis direction. This entire constitution is regarded as an integrated detector ring (referred to as a ring set or a unit) and arranged in a multilayered manner.

For the sake of explanation, detector rings equal in width W are supposed to be arranged in the number of D at a uniform interval of $\alpha$W ($0<\alpha\leq 1$), and $\alpha$ and D are supposed to be fixed in every step. FIG. 4 shows a case where D is fixed, for example, to 3.

As shown in step 1 of FIG. 4, a detector ring 11 constituted with detecting elements or detecting element blocks of width W is given as a unit [0], and an entire constitution in which units [0] in the number of D are arranged apart at an interval of αW is given as a unit [1] at a first level. A width W [1] of the unit [1] is to give (D+(D−1) α) W.

Next, as shown in step 2 of FIG. 4, an entire constitution in which the units [1] in the number of D are arranged apart at an interval of αW [1] is given as a unit [2] at a second level. A width W [2] of the unit [2] is to give $(D+(D-1)\alpha)^2$ W.

The above-described steps are repeated at a total number of N, and as shown in step N of FIG. 4, a unit [N] at an N level is obtained. In other words, detector rings corresponding to width $D^N$ W are able to cover a field-of-view $(D+(D-1)\alpha)^N$ W in the body axis direction.

Here, when $\{(D+(D-1)\alpha)/D\}^N$ is defined as a magnification for enlarging a field-of-view, for example, in the case of D=2 and α=0.5, if N is equal to 5, the magnification is to be approximately three times, if N is equal to 10, it is to be approximately 9 times, and if N is equal to 20, it is to be approximately 87 times.

Here, α is a parameter for adjusting a balance between the effects of enlarging an open-region clearance and a field-of-view in the body axis direction and the effects of reducing the sensitivity variation. In a range of 0<α≦1, a value may be changed in every unit or in every step. Where α is made smaller, a local reduction in sensitivity is suppressed, while the effects of enlarging the open-region clearance and the field-of-view in the body axis direction are reduced. On the contrary, where a is fixed to a maximum value which is 1, the open-region clearance and the field-of-view in the body axis direction are maximized, while the local reduction in sensitivity is emphasized.

FIG. 5 shows results obtained by examining a case where a is fixed (for example, α=0.5) and D is equal to 2, 3, 4 and 5, N is changed to have a relationship between the number of detector rings to be used $D^N$ and a field-of-view in the body axis direction to be accomplished $(D+(D-1)\alpha)^N$. Here, for the sake of convenience, W is equal to 1. Thereby, it is found that where D is equal to 2, the magnification is highest. According to an increase in the number of N, the magnification can be increased indefinitely.

In addition, W, D and α are changed within steps and between steps, thus making it possible to adjust the distribution of sensitivity.

The present invention which has been made on the basis of the above technical idea relates to a PET scanner in which detector rings are arranged in a multilayered manner so as to oppose each other in the body axis direction. In the PET scanner, a predetermined number of detector units, each of which is made up of a predetermined number of detector rings, are arrayed so as to give each other a clearance, and a first ring set in which the clearance is less than or equal to a mean value of widths of two detector units forming each clearance and a second ring set constituted with a predetermined number of detector units are arrayed apart so as to give a clearance which is less than or equal to a mean value of the width of the first ring set and that of the second ring set, thus imaging a field-of-view including the clearance and continuing in the body axis direction to an entire length of the first ring set and that of the second ring set. Thereby, the above object has been accomplished.

Further, a third ring set which internally houses at least the first ring set and the second ring set and a fourth ring set constituted with a predetermined number of detector units are arranged apart so as to give a clearance which is less than or equal to a mean value of the width of the third ring set and that of the fourth ring set, thereby imaging a field-of-view including the clearance and continuing in the body axis direction to an entire length of the third ring set and that of the fourth ring set. Thereby, the above object has been accomplished.

Here, at least one of the detector units may be a multiple ring-type detector.

Further, it is possible to include a plurality of the same ring sets.

Further, it is possible to include a plurality of ring sets which are different at least in one of the number of detector units constituting the ring set, a width of the detector unit and a clearance between the detector units.

Further, it is possible to change a dimension (width) of the ring set in the body axis direction and/or an interval between ring sets, depending on a ring set and/or between ring sets.

Further, it is possible to open a gantry at least partially in accordance with at least some of the clearances between the detector units or between the ring sets.

Further, at least some of the detector units or the ring sets may be structured so as to move in the body axis direction, thus making it possible to change at least some of the clearances.

Still further, a dimension (width) of detecting element blocks constituting the detector unit in the body axis direction may be made equal to a dimension (width) of the detector unit in the body axis direction.

In addition, it is possible that a predetermined number of detecting elements arranged apart so as to give a clearance equal in dimension to an interval between the detector units constitute an integrated detecting element block, and the detecting element blocks arranged in a ring shape constitute the ring set.

The present invention also provides a method for deciding an arrangement of detectors which includes a step in which a detector ring constituted with detectors or detecting element blocks of width W is given as a unit [0] and units [0] in the number of D [0] are arranged apart to give an interval of α[0]×W, thereby giving an entire constitution of securing a field-of-view in the body axis direction continuing over all in width W [1], which is referred to as a unit [1], a step in which units [1] in the number of D[1] are arranged so as to give an interval of α [1]×W [1], thereby giving an entire constitution of securing a field-of-view in the body axis direction continuing over all in width W [2], which is referred to as unit [2], and a step in which the above steps are repeated in the number of N to obtain a unit [N] in such a manner as to decide an arrangement of the detector rings in a PET scanner in which a plurality of detector units are arrayed so as to oppose each other, with a clearance kept in the body axis direction, thereby imaging a field-of-view including the clearance and continuing in the body axis direction.

It is noted that, as being superficially similar to the present invention, a technical idea in which detectors are arranged sparsely, with a clearance kept, thereby coincidence lines are sampled less frequently to increase the uniformity and also to expand a field-of-view region has been proposed (refer to Japanese Published Unexamined Patent Application No. Hei 9-211130 and Japanese Published Unexamined Patent Application No. 2001-141827). In particular, Japanese Published Unexamined Patent Application No. Hei-9-211130 has clearly described that when detectors of width W of a light-receiving surface are arrayed in one direction, a distance between a central point of the light-receiving surface of a detector on one end and a central point of the light-receiving surface of a next detector thereof is given as L, and a distance between central points of light-receiving surfaces of any given mutually adjacent detectors excluding detectors at ends is given as L', formulae, W≦L≦2W and L'=2L are provided. A maximum value of L' is 4W, which means that a distance between the light-receiving surfaces of mutually adjacent detectors from one end to the other end is 3W.

However, the above-described technical idea has been made on the basis of a positron imaging device for planar imaging and does not mention at all about its application to a PET scanner which is a tomograph fundamentally different in the principle of imaging. On the assumption that detectors are sparsely arranged on a ring according to this technical idea, coincidence lines necessary for image reconstruction are lost to inevitably result in deterioration of image quality. Alternatively, on the assumption that detectors are densely arranged on a ring but this technical idea is applied only in the body axis direction, thereby providing a PET scanner in which individual single-ring type detectors are arranged sparsely, a field-of-view in the body axis direction is enlarged up to approximately two times, and also in order to obtain a clinically significant resolution in the body axis direction, it is necessary to make W small to such an extent of several millimeters. As a result, a maximum value of the thus obtained clearance (3W) is small and not beneficial.

Since an open-type PET scanner is able to provide medical treatment from an open space, it is expected to make a PET diagnosis in a patient under medical care which would be otherwise impossible. The present invention is able to enlarge an open-region clearance and a field-of-view in the body axis direction without changing the total number of detectors. Enlargement of a maximum value of the open-region clearance means that if the open-region clearance is the same, the distribution of sensitivity can be overlapped more to effectively suppress a local reduction in sensitivity. Further, a field-of-view is enlarged, by which a PET scanner with a whole-body field-of-view capable of making a whole-body diagnosis at one time is made available at a relatively low cost. A PET scanner with a whole-body field-of-view is able to promote the development of new drugs efficiently and, therefore, indispensable in promoting micro-dosing tests which have gained attention as a method for selecting candidate compounds exhibiting optimal pharmacokinetics for humans by dosing a trace amount of compounds at an earlier stage of drug development.

BRIEF DESCRIPTION OF THE DRAWINGS

FIG. 11($a$) is a drawing showing the distribution of sensitivity in Embodiment 4 of the present invention and FIG. 11($b$) is a drawing showing the distribution of sensitivity in Embodiment 5 of the present invention.

FIG. 15($a$) is a drawing showing the result of optimization by an open-type PET scanner before applying a multilayered arrangement (G0=150 mm), FIG. 15($b$) is a drawing showing the result of optimization under the condition of G0=150 mm, Weva=150 mm and FIG. 15($c$) is a drawing showing the result of optimization under the condition of G0=200 mm, Weva=500 mm.

BEST MODE FOR CARRYING OUT THE INVENTION

Figure 1:
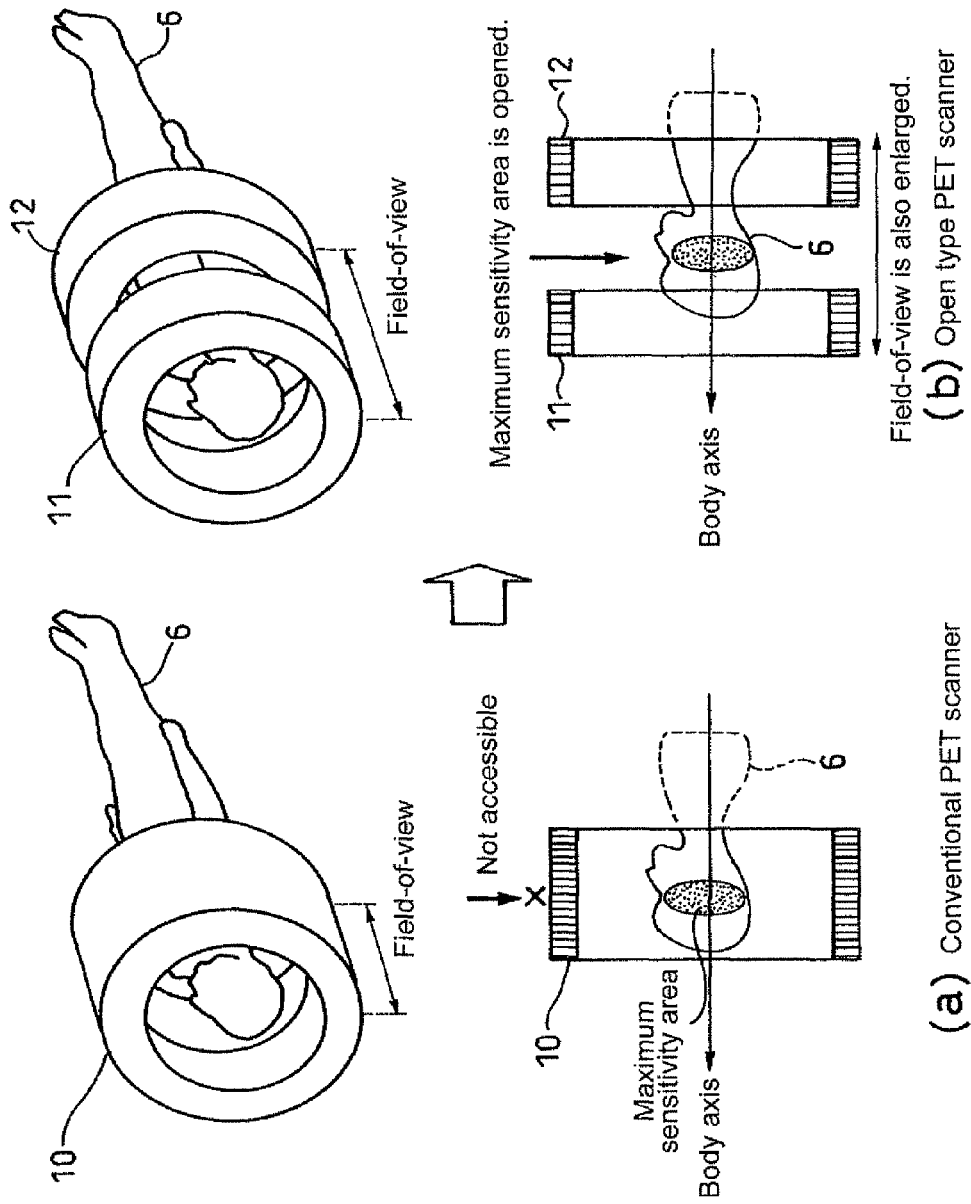
FIG. 1($a$) covers a perspective view and a cross sectional view showing a constitution of a conventional general PET scanner and FIG. 1($b$) covers a perspective view and a cross sectional view showing a constitution of an open-type PET scanner before applying a multilayered arrangement which was proposed previously by the applicant.
Figure 2:
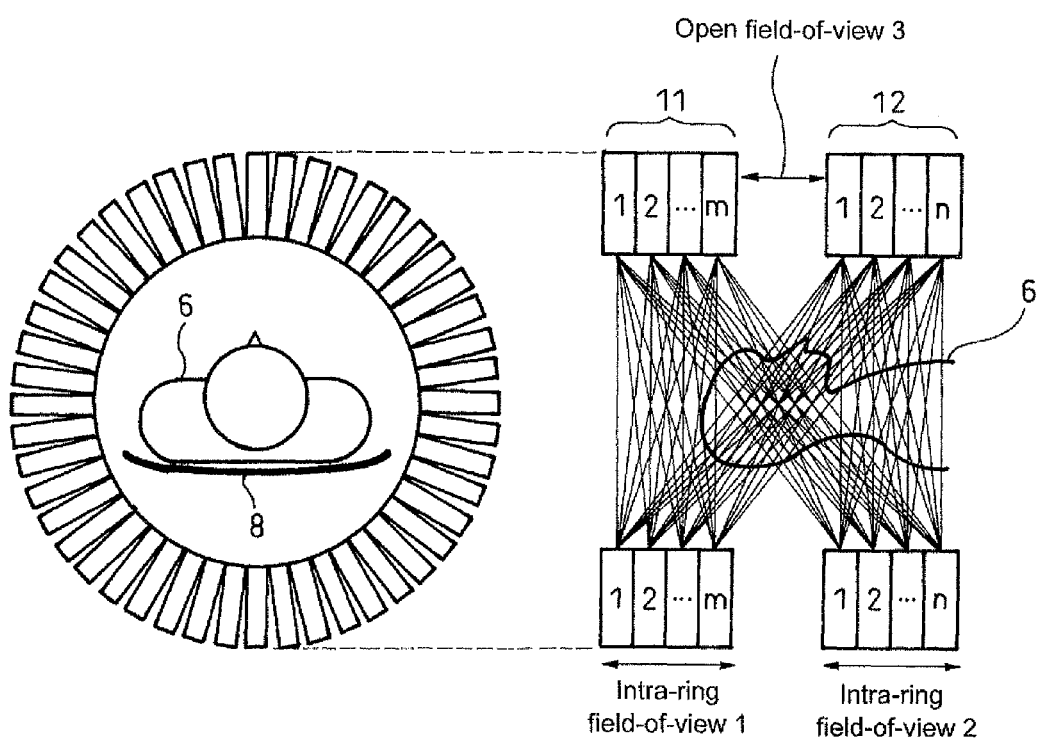
FIG. 2 is a cross sectional view showing the principle of image reconstruction in an open-type PET scanner.
Figure 3:
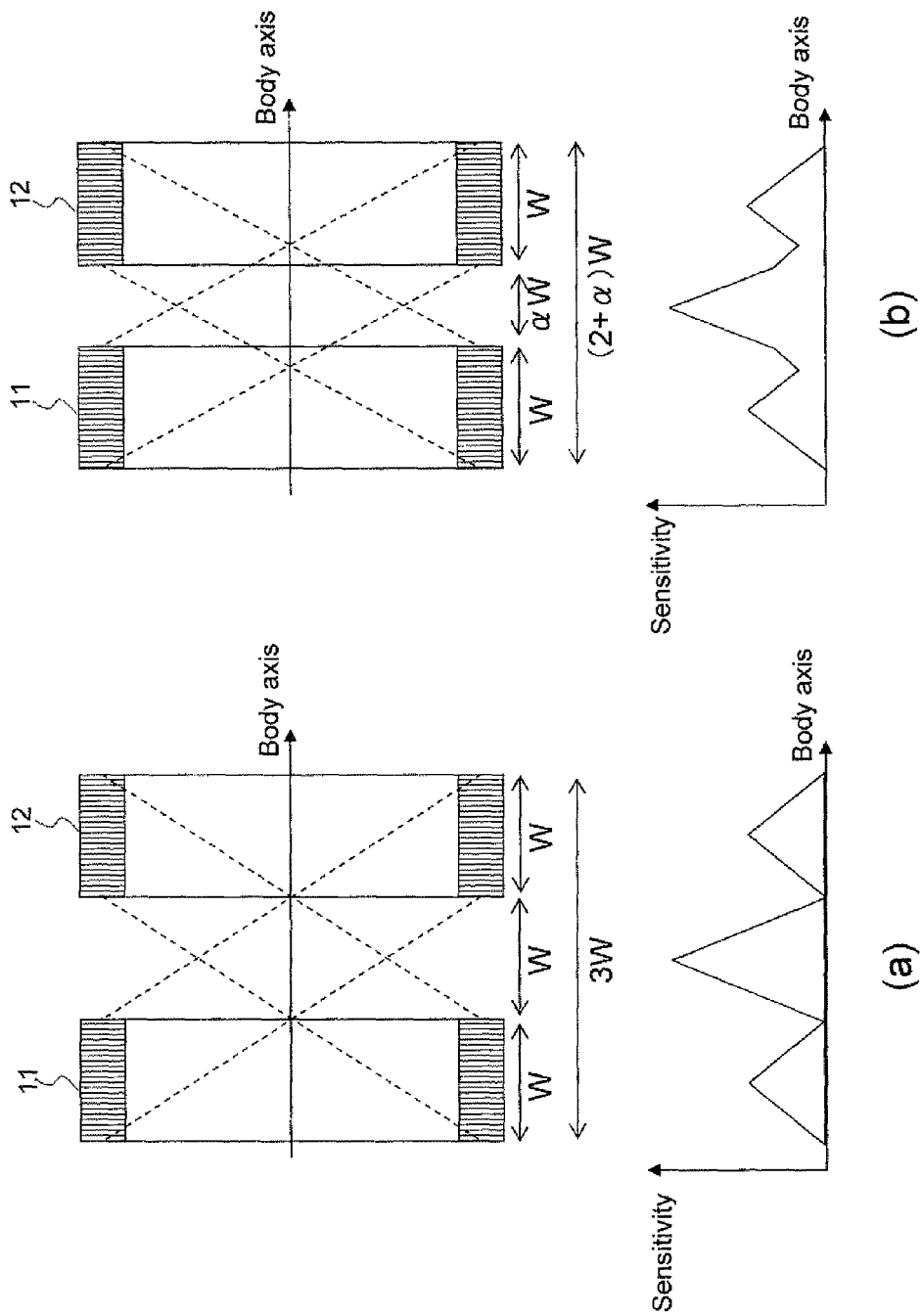
FIG. 3 covers cross sectional views and graphs showing a relationship between the open-region clearance of an open-type PET scanner and the sensitivity.
Figure 4:
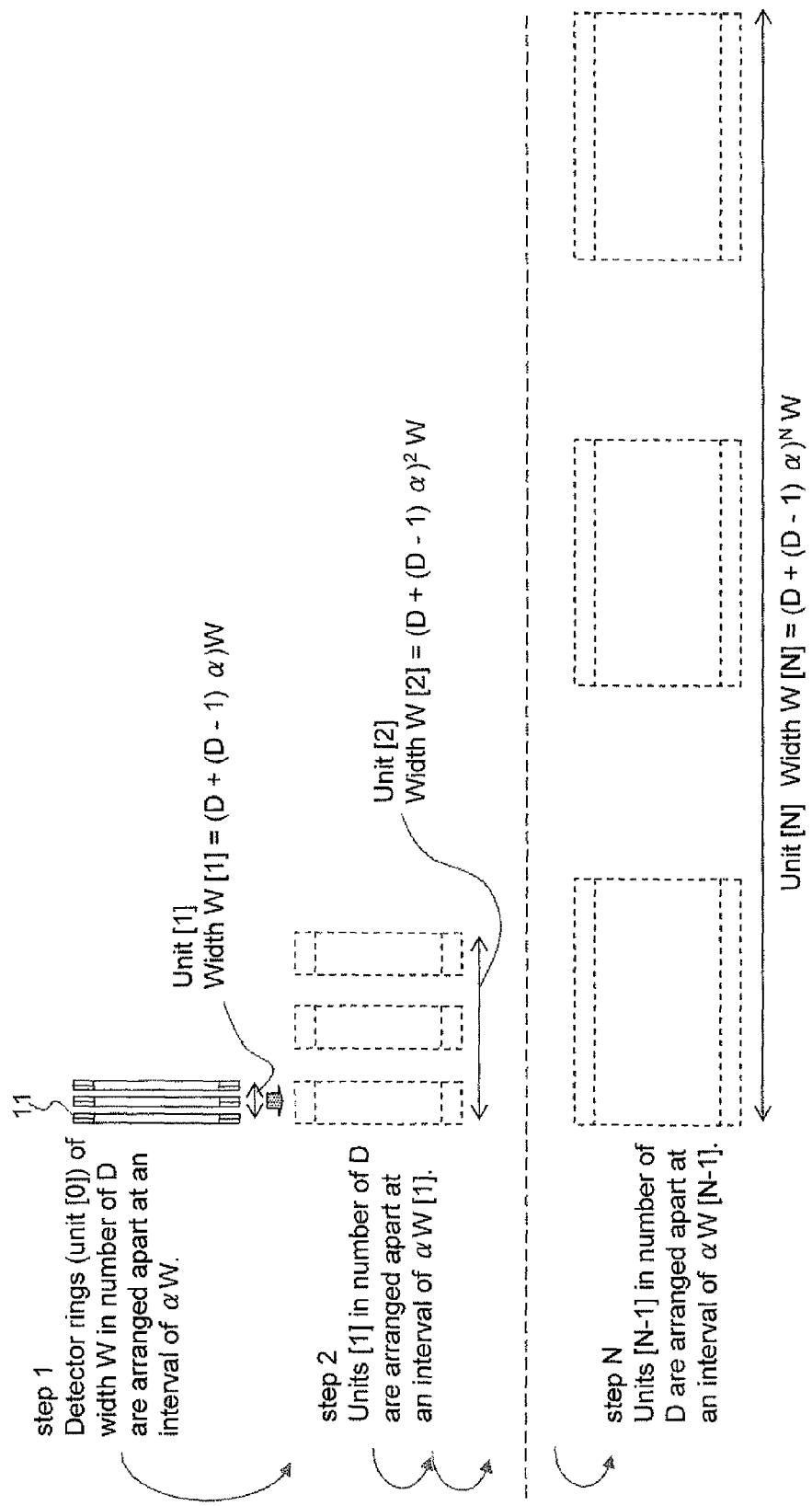
FIG. 4 is a cross sectional view showing the principle of the present invention.

Hereinafter, a detailed explanation will be made for embodiments of the present invention by referring to the drawings.

Figure 6:
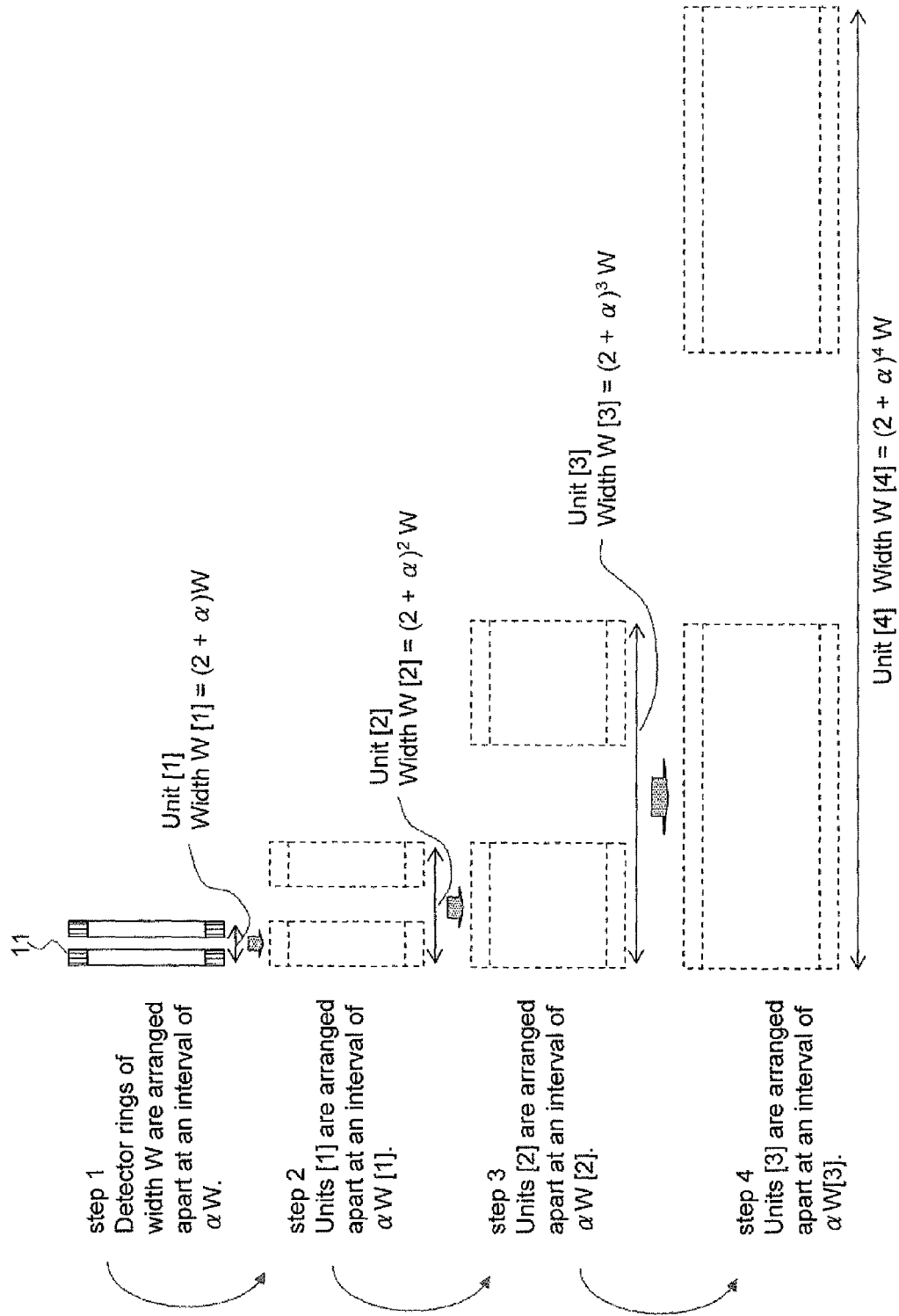
FIG. 6 is a cross sectional view showing how to decide an arrangement of detectors of Embodiment 1 of the present invention.

FIG. 6 shows how to decide an arrangement of detectors of Embodiment 1 of the present invention where a detector ring width W is made equal and $\alpha$ is fixed under the conditions of D=2 and N=4.

First, in step 1, a detector ring 11 of width W is given as a unit [0] and an entire constitution in which two units [0] are arranged apart at an interval of $\alpha W$ ($0<\alpha \leq 1$) is given as a unit [1] at a first level. A width W [1] of this unit [1] is expressed as $(2+\alpha)$ W.

Then, in step 2, an entire constitution in which two units [1] are arranged apart at an interval of $\alpha W$ [1] is given as a unit [2] at a second level. A width W [2] of this unit [2] is expressed as $(2+\alpha)^2$ W.

The above steps are repeated four times all together to obtain a unit [4] at a level four in step 4. In other words, detector rings corresponding to width $2^4 W$ makes it possible to cover a field-of-view of $(2+\alpha)^4$ W in the body axis direction.

Figure 7:
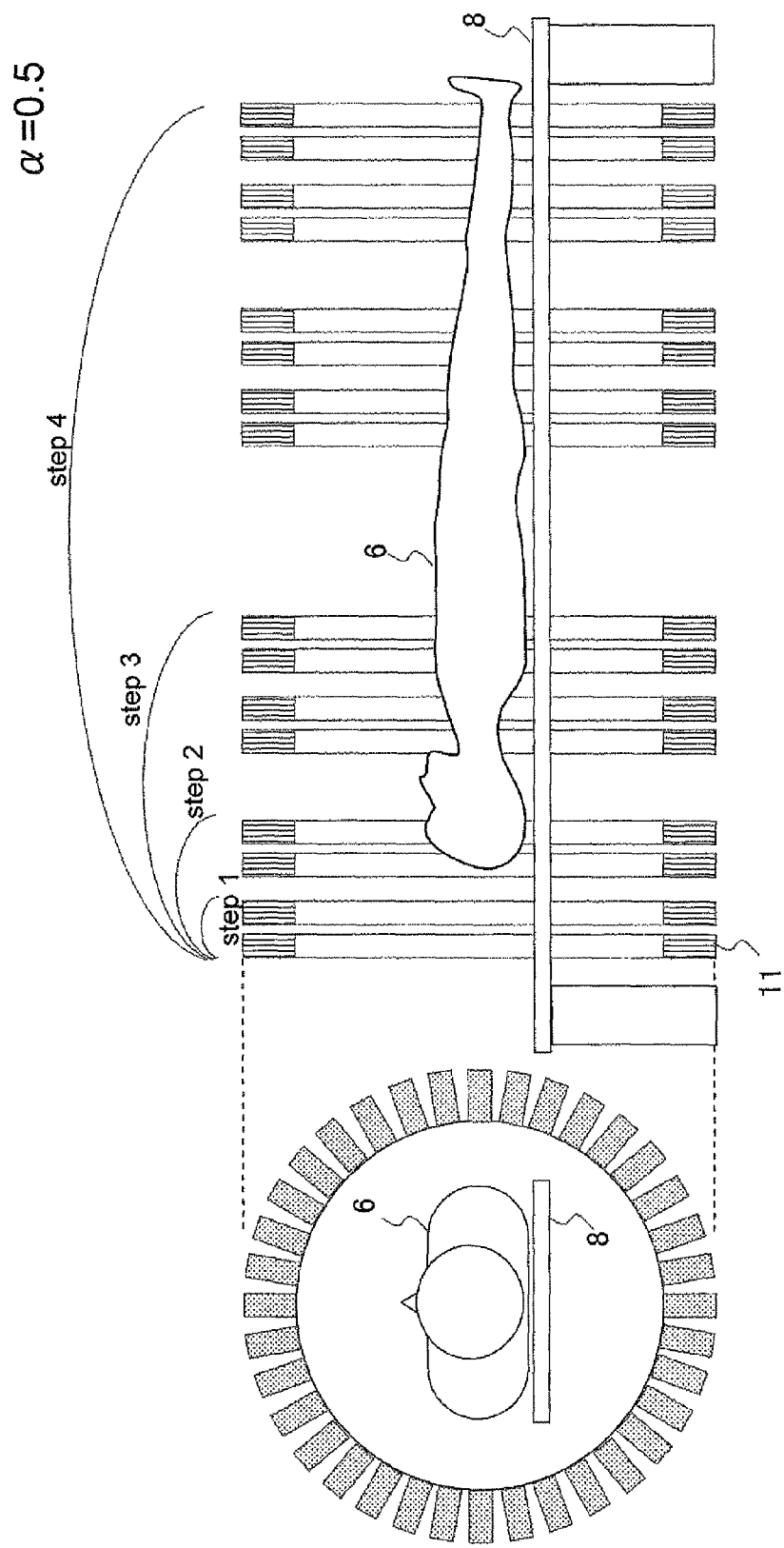
FIG. 7 covers a cross sectional view and a side elevational view showing an arrangement of the detectors of Embodiment 2 of the present invention.

Further, FIG. 7 covers drawings schematically showing an arrangement of detectors of Embodiment 2 of the present invention where α is equal to 0.5. In this instance, since a field-of-view of $2.5^4$ W in the body axis direction is obtained from a detector ring with a total width of $2^4$ W, the magnification is $(2.5/2)^4 \approx 2.4$.

Next, a simulation was conducted by using a computer in which, on the basis of a commercially available PET scanner, the scanner constituted with 48 detector rings (width of 4.8 mm) having 576 detecting elements (scintillators) on a circumference the diameter of which is 827 mm was modeled. A numerical phantom was that which contains 63 spots with a diameter of 4.0 mm in a uniform cylindrical radiation source and a contrast ratio of the cylinder to the spot was 1:5.

Figure 8:
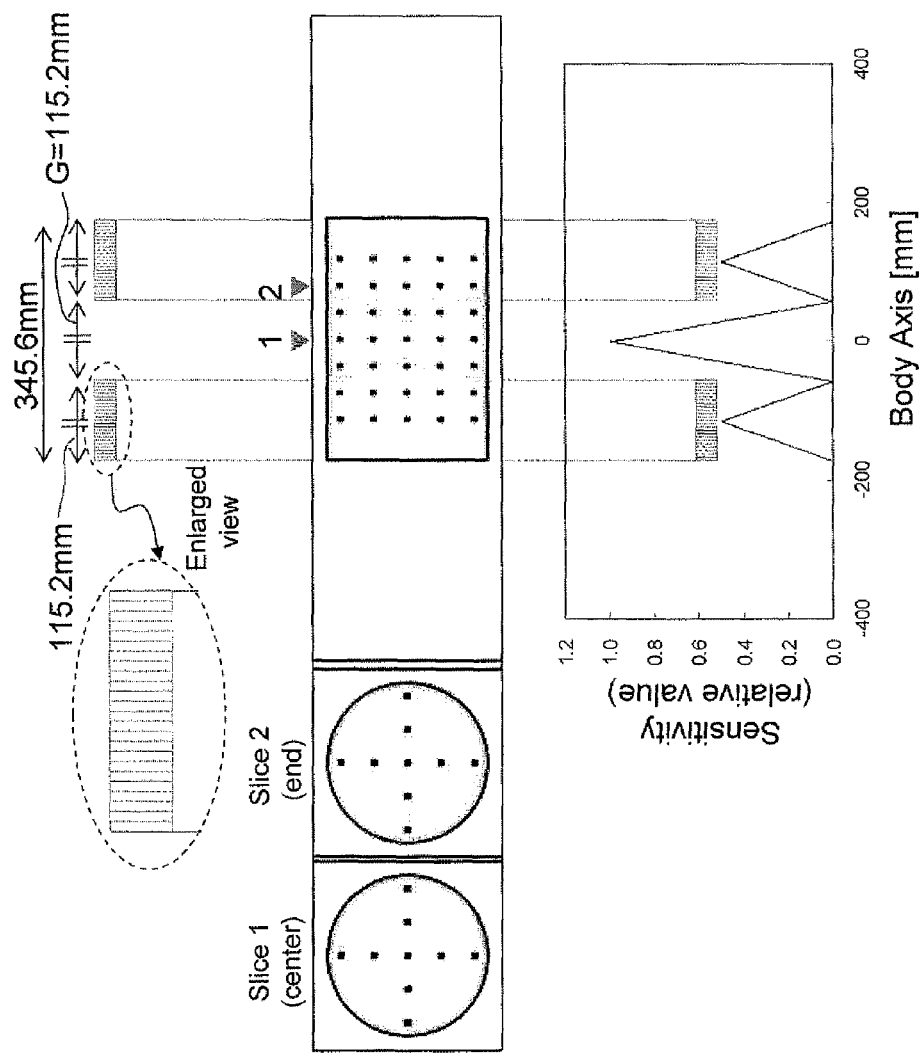
FIG. 8 is a drawing showing a result of simulation where an open-type PET scanner before applying a multilayered arrangement was used to maximize an open region.

FIG. 8 shows a result obtained where the open-type PET scanner before applying a multilayered arrangement which was proposed previously by the applicant was used to maximize an open-region clearance (α=1). More specifically, 24 detector rings are given as a unit (W=115.2 mm) and two units are arranged apart to give a clearance of 115.2 mm (corresponding to 24 rings). A field-of-view in the body axis direction is 345.6 mm. The cross sectional images on display were subjected to contour extraction processing for enhancing the visibility. The graph below FIG. 8 shows a result of the distribution of sensitivity on the body axis, from which a drastic reduction in sensitivity at both ends of an open region is found.

Figure 9:
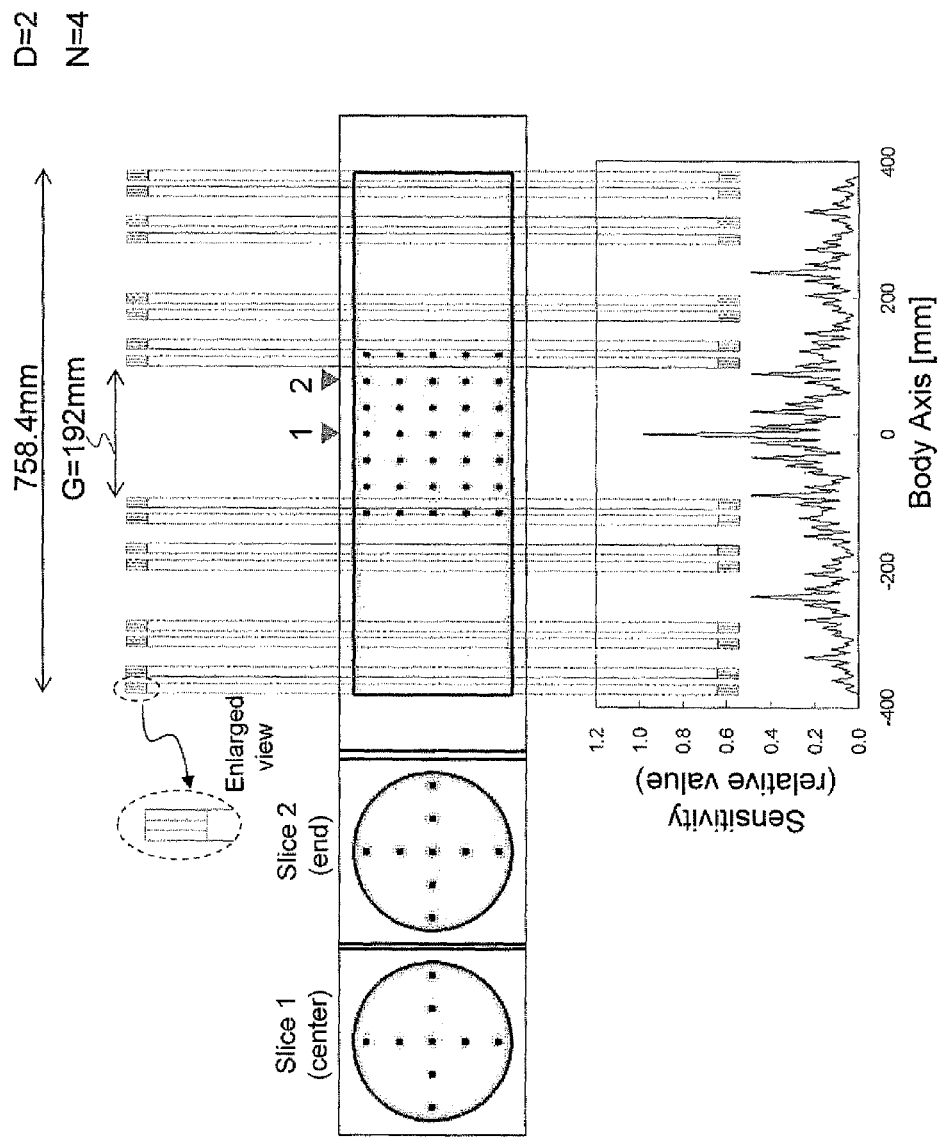
FIG. 9 is a drawing showing a result of simulation obtained in Embodiment 3 of the present invention.

On the other hand, FIG. 9 shows a result obtained in Embodiment 3 of the open-type PET scanner after a multilayered arrangement in the present invention where three detector rings are given as a unit [0] (W=14.4 mm) and the open-type PET scanner was arranged in a multilayered manner to arrange detectors under the conditions of D=2, α=2/3 and N=4. The number of detector rings used is $3 \times D^N = 3 \times 2^4 = 48$ and in agreement with the example shown in FIG. 8. Thereby, an open region of 192 mm (corresponding to 40 rings) is secured at the center of the scanner and a field-of-view of 758.4 mm in the body axis direction is secured all together. Further, due to the fact that α adopted here is smaller than that in FIG. 8, there is no drastic reduction in sensitivity as found in FIG. 8.

Figure 10:
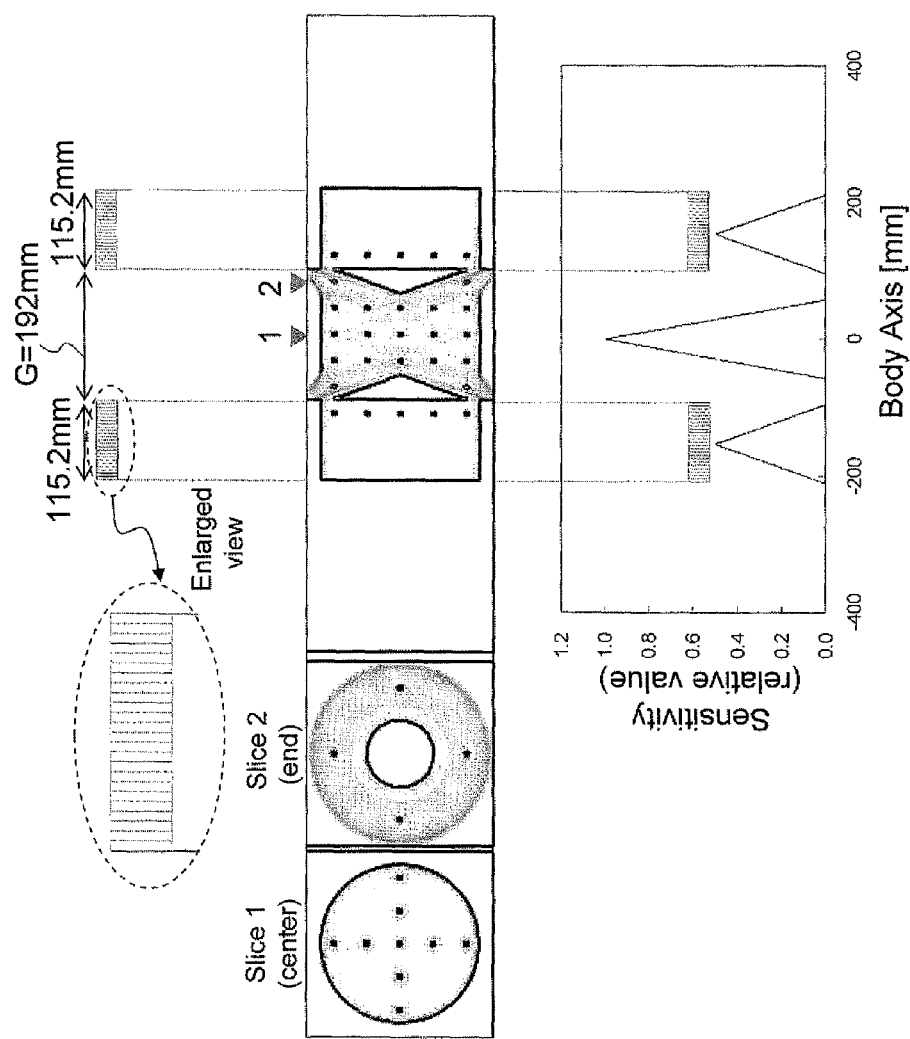
FIG. 10 is a drawing showing a result of simulation where the open-type PET scanner before applying a multilayered arrangement was used to secure an open region of 192 mm as with the case of FIG. 9.

FIG. 10 shows a result of simulation where the open-type PET scanner before applying a multilayered arrangement was used in an attempt to secure an open region of 192 mm (corresponding to 40 rings) as with FIG. 9. A region of no sensitivity appeared at each end of the open region demonstrates a failure in proper imaging.

FIG. 11 shows the distribution of sensitivity where, as an example other than that of D=2, three detector rings are given as a unit [0] and detectors are arranged under the conditions of W=14.4 mm, α=2/3 and N=2. FIG. 11(a) shows Embodiment 4 where D is equal to 3, while FIG. 11(b) shows Embodiment 5 where D is equal to 4. In Embodiment 4, a total number of detector rings to be used is 27, a maximum gap is 43.2 mm (corresponding to 9 rings) and a total field-of-view in the body axis direction is 273.6 mm (corresponding to 57 rings). In Embodiment 5, a total number of detector rings to be used is 48, a maximum gap is 57.6 mm (corresponding to 12 rings) and a total field-of-view in the body axis direction is 518.4 mm (corresponding to 108 rings).

Figure 12:
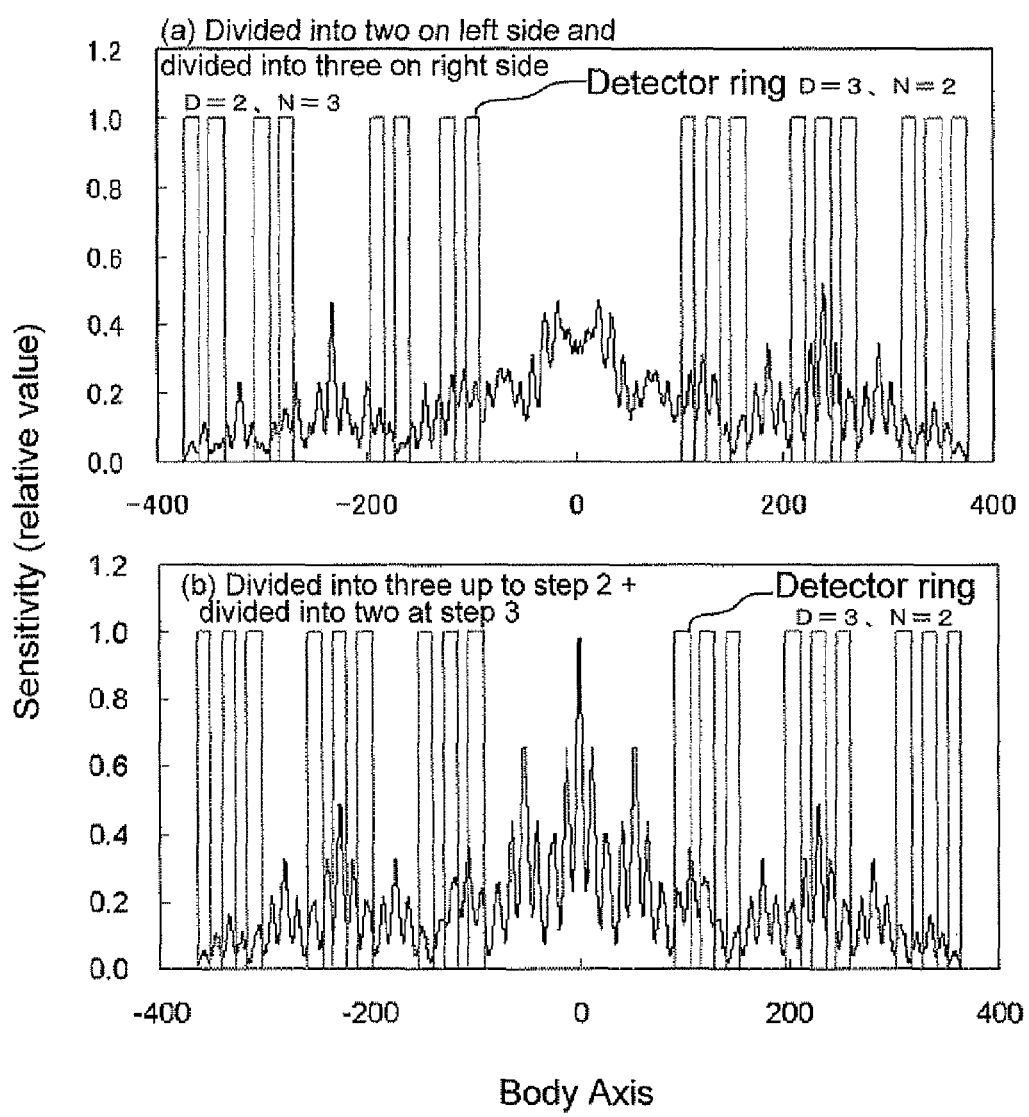
FIG. 12($a$) is a drawing showing the distribution of sensitivity in Embodiment 6 of the present invention and FIG. 12($b$) is a drawing showing the distribution of sensitivity in Embodiment 7 of the present invention.

FIG. 12 shows examples where different values of D are combined. FIG. 12(a) shows a result of Embodiment 6 in which, as an example where an arrangement of detectors is changed depending on the right side and the left side, an arrangement (D=2, α=2/3, N=3) is combined with an arrangement (D=3, α=2/3, N=2). The detectors are arranged in an asymmetric manner on both sides, thereby eliminating the concentration of sensitivity at the center of the scanner to obtain a relatively flat distribution of sensitivity at an open region. FIG. 12(b) shows the distribution of sensitivity in Embodiment 7 where up to step 2, D is equal to 3 and at step 3, D is equal to 2. In Embodiment 6, a total number of detector rings to be used is 51, a maximum gap is 192 mm (corresponding to 40 rings) and a total field-of-view in the body axis direction is 748.8 mm (corresponding to 156 rings). In Embodiment 7, a total number of detector rings to be used is 54, a maximum gap is 182.4 mm (corresponding to 38 rings) and a total field-of-view in the body axis direction is 729.6 mm (corresponding to 152 rings).

Figure 13:
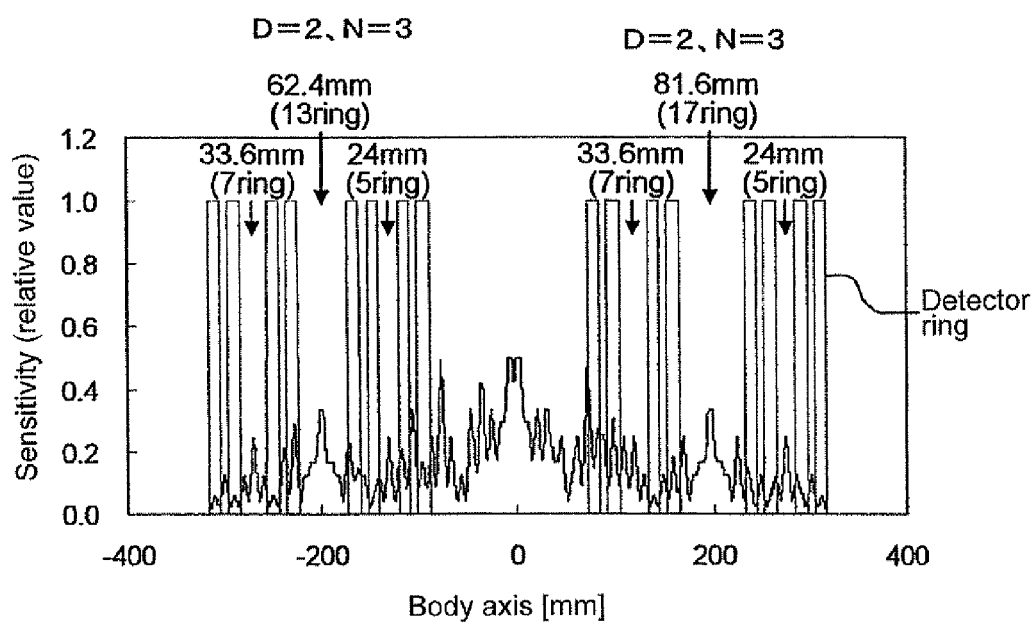
FIG. 13 is a drawing showing the distribution of sensitivity in Embodiment 8 of the present invention.

FIG. 13 shows Embodiment 8 where D and W are fixed and α, that is, a clearance (gap) between units is finely adjusted inside a step and between steps, thereby reducing the concentration of sensitivity at the center of the scanner.

More specifically, under the conditions of D=2, W=14.4 mm (corresponding to 3 rings), and N=4, a gap in step 1 is fixed to 9.6 mm (corresponding to 2 rings) but a gap in step 2 is either 33.6 mm (corresponding to 7 rings) or 24 mm (corresponding to 5 rings), and a gap in step 3 is either 62.4 mm (corresponding to 13 rings) or 81.6 mm (corresponding to 17 rings). A total number of detector rings to be used in Embodiment 8 is 48, a maximum gap is 192 mm (corresponding to 40 rings), and a total field-of-view in the body axis direction is 758.4 mm (corresponding to 158 rings).

Figure 14:
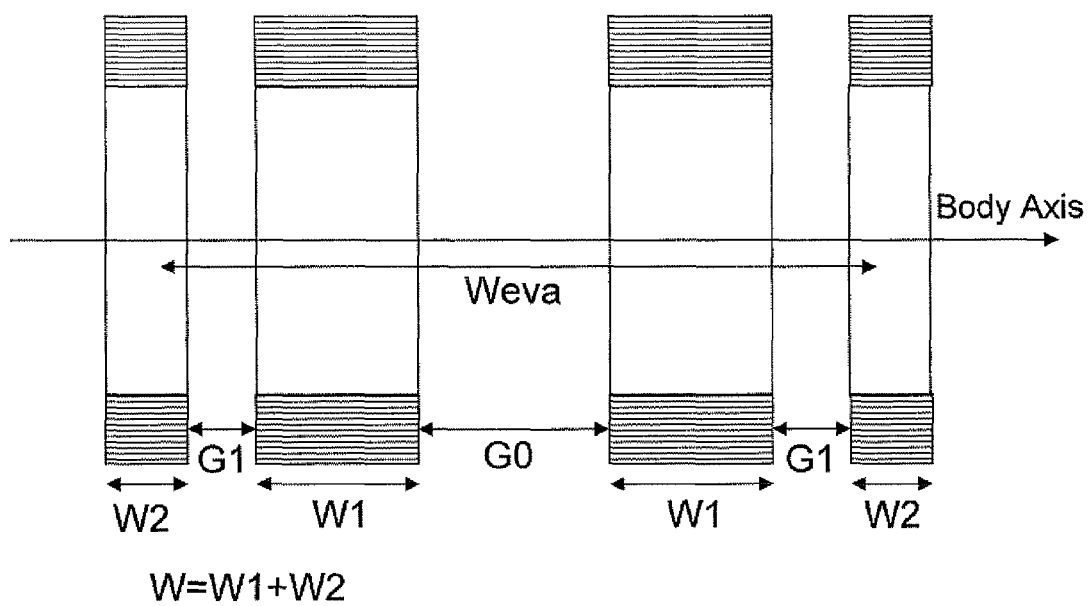
FIG. 14 is a cross sectional view showing a constitution of an object which was investigated for the distribution of sensitivity.

Next, an example where under fixed conditions of D=2 and N=2, W and α are changed is shown. More specifically, in the system shown in FIG. 14, a total value of width W of detector rings was fixed to 2W=300 mm, and W1, W2 (between 0 and W) and G1 (between 0 and G0) were changed by every one mm at a specified sensitivity region clearance G0 to calculate the distribution of sensitivity (W=W1+W2), thereby examining a combination where the distribution of sensitivity in the body axis direction was minimized. A variation of the distribution of sensitivity was given as a standard deviation within a specified evaluation range of Weva.

FIG. 15(a) shows a result obtained by using an open-type PET scanner before applying a multilayered arrangement to maximize an open region clearance as a reference and the open region clearance of 150 mm which is the same as the width W of a detector ring is obtained. FIG. 15(b) shows a result obtained by optimizing W1, W2 and G1 so that a variation of the distribution of sensitivity is minimized with respect to an open region clearance G0=150 mm also in a range of Weva=150 mm. FIG. 15(c) shows a result obtained by optimizing W1, W2 and G1 so that the open region clearance is to give G0=200 mm. without changing a total value of width of detector rings to be used and a variation of the distribution of sensitivity is minimized in a range of Weva=500 mm.

Figure 16:
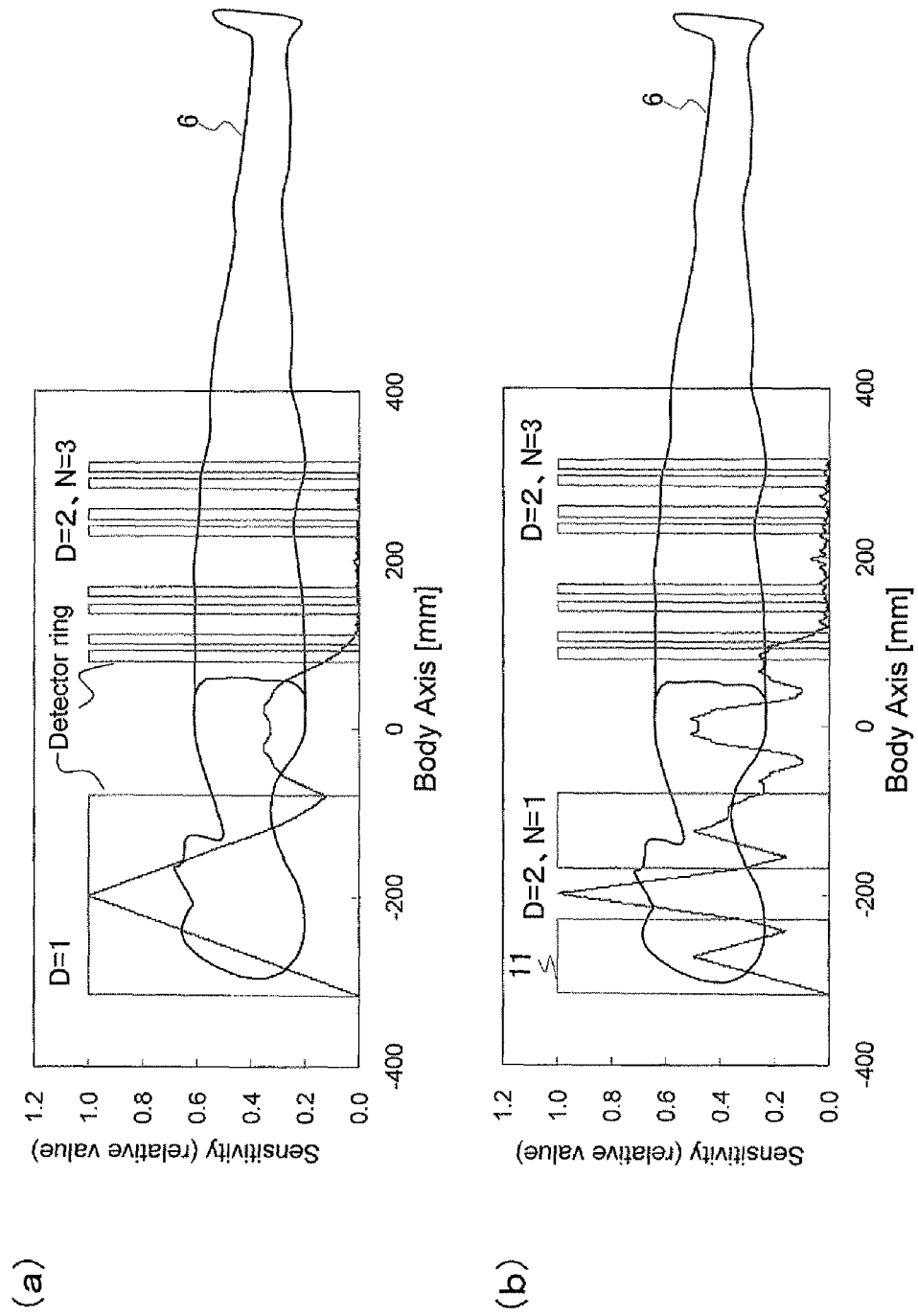
FIG. 16($a$) is a drawing showing the distribution of sensitivity in Embodiment 9 of the present invention and FIG. 16($b$) is a drawing showing the distribution of sensitivity in Embodiment 10 of the present invention.

In any of the previously described embodiments, only a ring set is used. However, where, for example, the sensitivity at the head is desired to be enhanced, as described in Embodiment 9 (a combination of D=1 on the left side, and D=2, N=3 on the right side) shown in FIG. 16(a), a detector ring which is not divided at the head may be provided. As described in Embodiment 10 (a combination of D=2, N=1, on the left side, and D=2, N=3 on the right side) shown in FIG. 16(b), the number of divisions at the head can be made smaller than on the side of the trunk.

Figure 17:
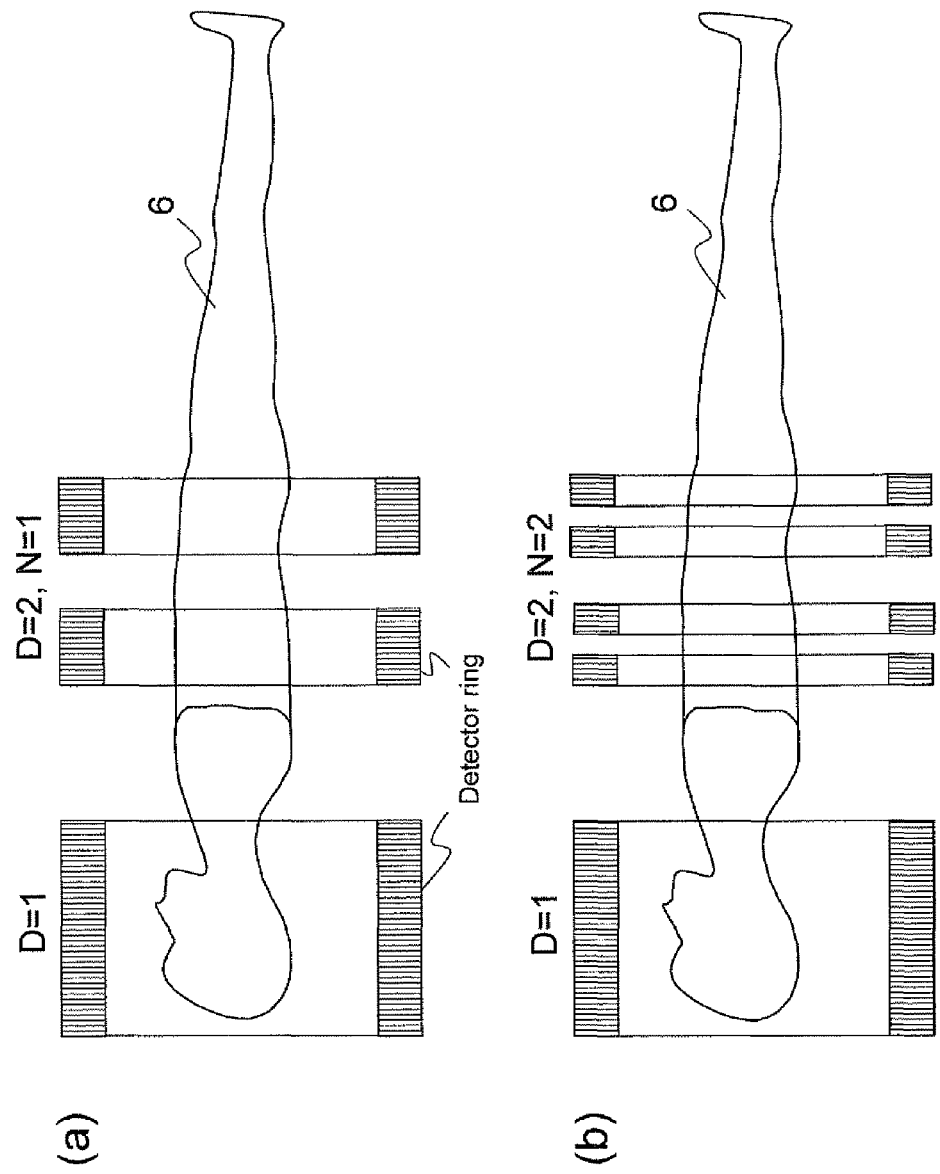
FIG. 17($a$) is a drawing showing a constitution of Embodiment 11 of the present invention and FIG. 17($b$) is a drawing showing a constitution of Embodiment 12 of the present invention.

Further, as described in Embodiment 11 (a combination of D=1 on the left side, and D=2, N=1 on the right side) shown in FIG. 17(a) and as described in Embodiment 12 (a combination of D=1 on the left side and D=2, N=2 on the right side) shown in FIG. 17(b), one of the ring sets (on the right side in the drawing) can be made into one set or two sets.

Figure 5:
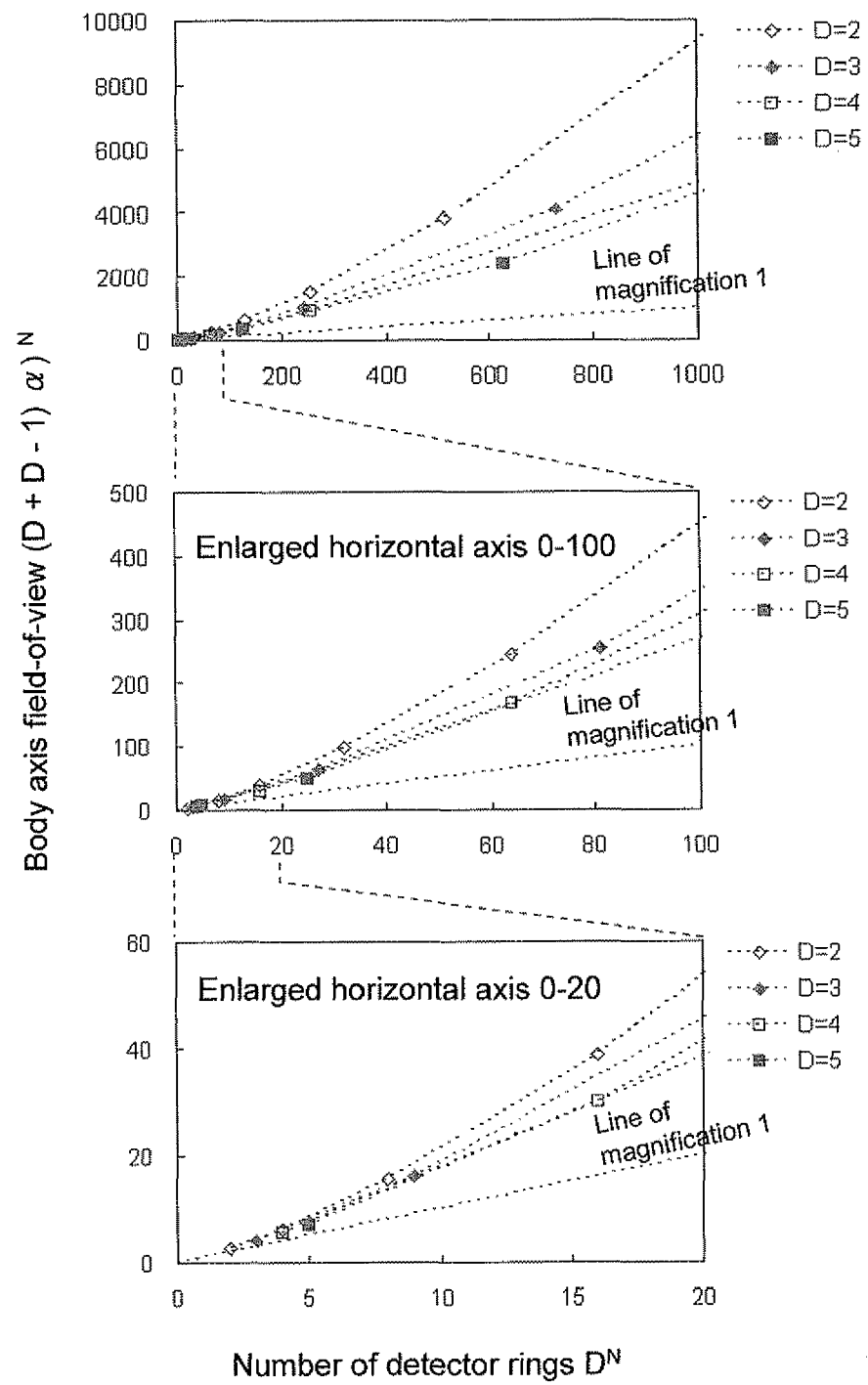
FIG. 5 covers graphs showing examples of relationships between the number of detector rings and a field-of-view in the body axis direction of the present invention.

From the previously described FIG. 5, it is apparent that a field-of-view enlargement and an enlarged magnification of an open region clearance in the present invention are made greater as the number of detector rings is increased. In other words, on the assumption that a total number of detecting elements is the same, a smaller number of detecting elements constituting a unit [0] is able to increase a final enlarged magnification. PET detectors include not only a conventional scintillation detector but also a semiconductor detector in which a cadmium telluride (CdTe) semiconductor element and others are used. Originally, the semiconductor detector has independent detecting elements, thereby making it easer to constitute a unit [0] with a small number of detecting element rings (one in an extreme case).

Figure 18:
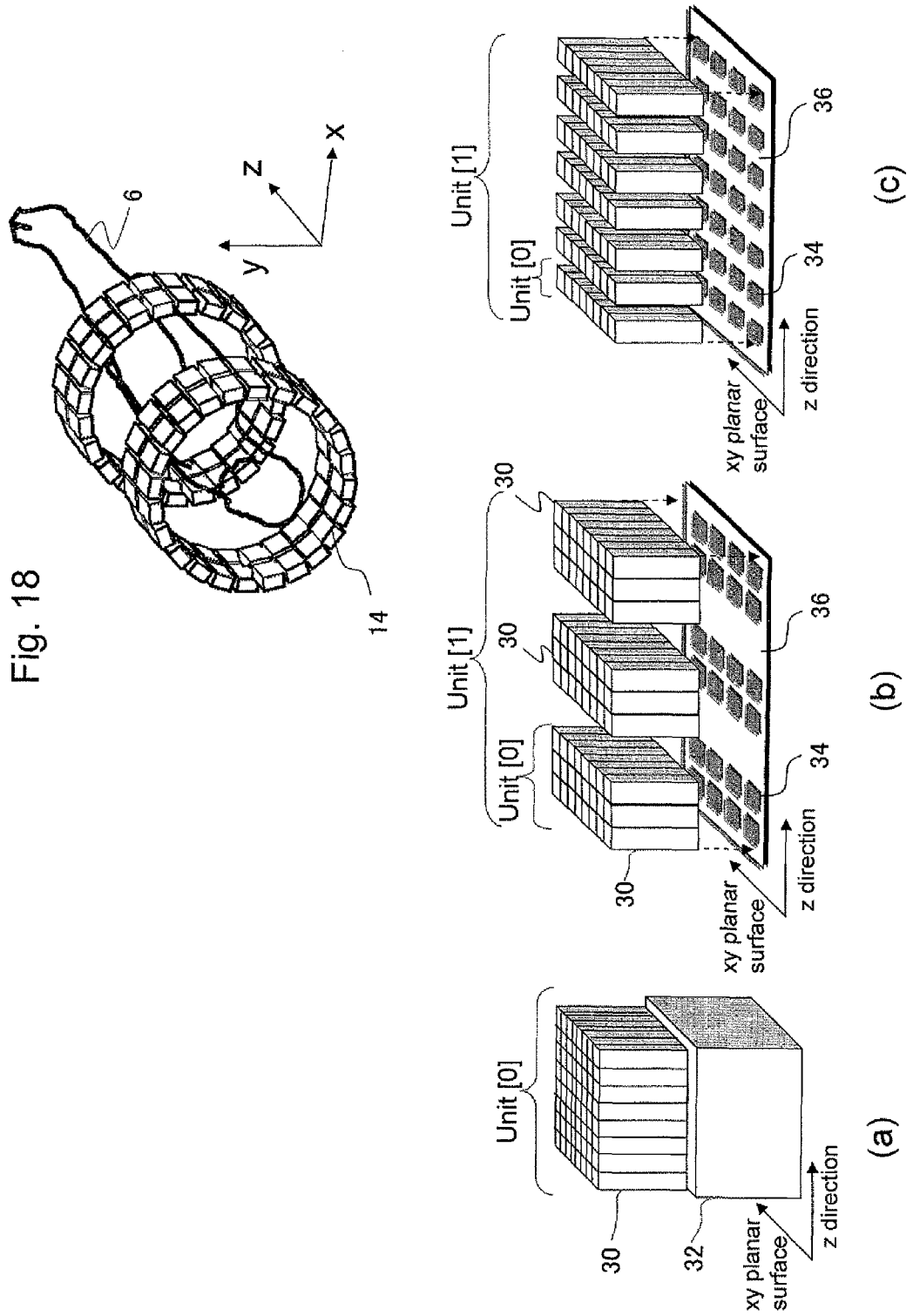
FIG. 18 covers perspective views showing constitution examples of detecting element blocks which constitute a detector ring.

As illustrated in FIG. 18(a), the scintillation detector is constituted with scintillators 30 and a photo detector (for example, a photomultiplier tube 32). And, as the photo detector, in addition to a conventional photomultiplier tube 32, a semiconductor photo detector such as an avalanche photodiode (APD) has gained attention. In the case of the photomultiplier tube, the detecting element block as shown in FIG. 18(a) is a minimum unit of constituting a unit [0]. In this instance, a dimension of the detecting element block in the body axis direction is a dimension of the unit [0] in the body axis direction. However, since there is a structural limit in downsizing the photomultiplier, it is difficult to downsize the detecting element block. Several detecting element rings or ultimately one detecting element ring may be given as a unit [0] and a plurality of units [0] can be loaded on the photomultiplier tube, with a clearance kept, thus making it possible to give the detecting element block as a unit [1]. However, the photomultiplier is not efficient in utilizing a light-receiving surface.

On the other hand, in the semiconductor photo detector, photo detecting elements 34 can be arranged on a substrate 36 in a relatively free manner. Therefore, as shown in FIG. 18(b) and (c), it is possible that several detecting element rings or ultimately one detecting element ring is given as a unit [0] and a plurality of units [0] are constituted integrally so that a clearance of the unit [0] is adjusted to an interval of the light receiving element 34 on the substrate 36. A relationship between the detecting elements and the light receiving elements in the unit [0] is ideally to be connected on a one-to-one basis. However, as shown in FIG. 18(b) and (c), the number of light receiving elements may be made smaller than that of the detecting elements, thereby making it possible to simplify a constitution of the detectors. In the cases of FIG. 18(b) and (c), the detecting element block 14 corresponds to the unit [1].

Figure 19:
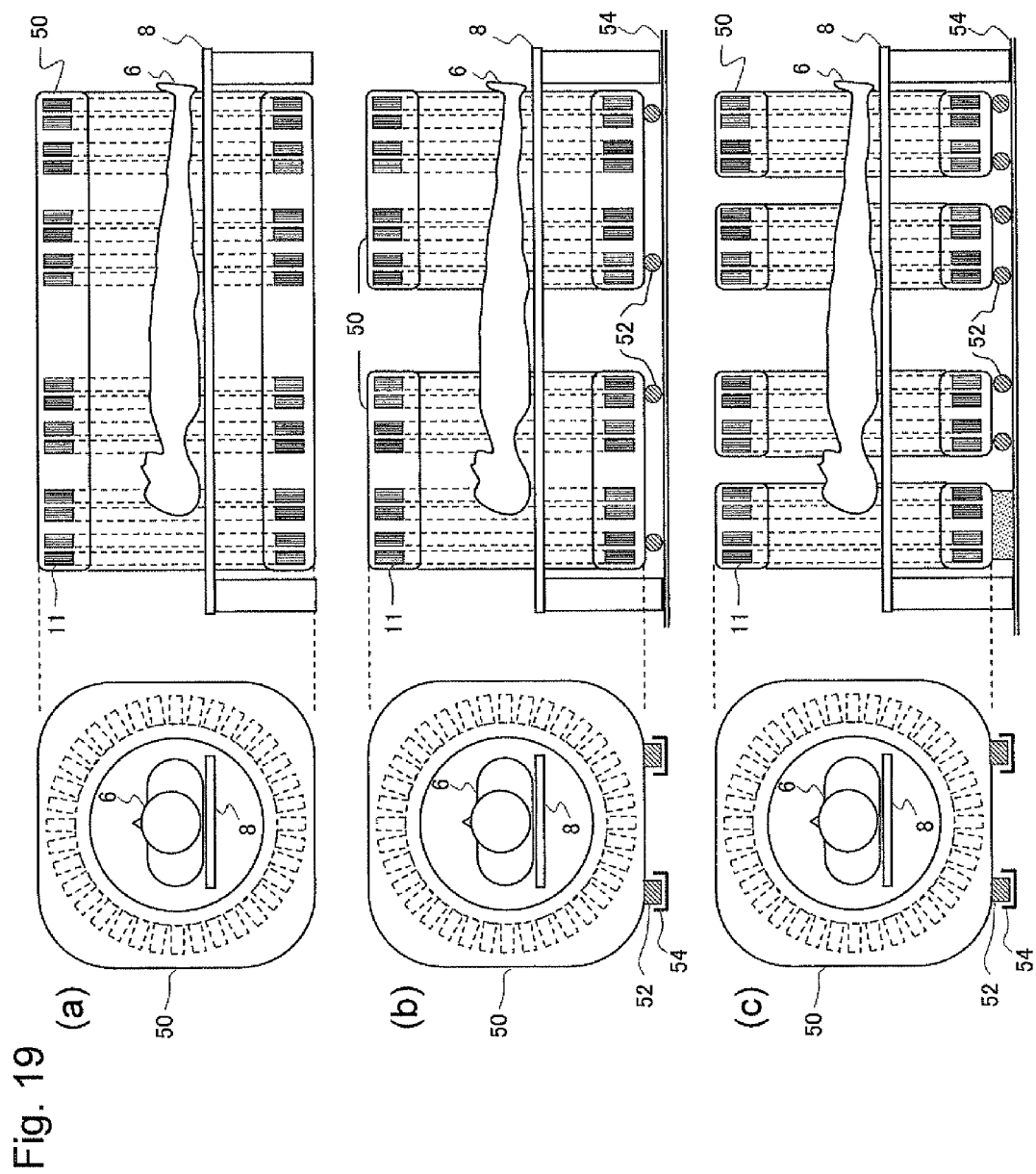
FIG. 19($a$) is a drawing showing the constitution of Embodiment 13 of the present invention, FIG. 19($b$) is a drawing showing the constitution of Embodiment 14 of the present invention and FIG. 19($c$) is a drawing showing the constitution of Embodiment 15 of the present invention.

In addition, the present invention is advantageous in enlarging a field-of-view in the body axis direction, while reducing the cost of the scanner, not only in an open-type PET scanner but also in a conventional non-open-type PET scanner. Embodiment 13 shown in FIG. 19(a) shows a constitution of a non-open-type PET scanner in which detectors are arranged inside an integrated long tunnel-shaped gantry 50. Embodiment 14 shown in FIG. 19(b) shows a constitution of an open-type PET scanner in which the gantry 50 is divided according to a maximum clearance, thereby having a physically opened field-of-view region. Further, Embodiment 15 shown in FIG. 19(c) shows a constitution of an open-type PET scanner in which the gantry 50 is divided according to a total of three clearances including a maximum clearance and second largest clearances, thereby having three open field-of-views.

Here, the gantry 50 may be fixed on the floor surface. At least some of the detector units or ring sets are structured so as to move in the body axis direction, allowing a clearance to change in a range of $0<\alpha\leq 1$, thus making it possible to change open region clearances depending on a clinical application and finely adjust the distribution of sensitivity depending on an object to be examined. In the embodiments shown in FIGS. 19(b) and 19(c), wheels 52 under the gantry are set on a rail 54 on the floor surface, moving a part or a whole of the gantry in the body axis direction, thereby allowing the open region clearances to change.

In addition, in any of the previously described embodiments, a cross section of the detector ring in the body axis direction is given as a circular shape. However, the cross section of the detector ring is not limited thereto but may be in an oval or a rectangular shape.

Further, objects to be examined are not limited to humans but may include animals.

Industrial Applicability

The present invention is a PET scanner in which detector rings are arrayed in a multilayered manner so as to oppose each other in the body axis direction. In an open-type PET scanner in which a predetermined number of detector units, each of which is made up of a predetermined number of detector rings, are arrayed apart to give each other a clearance, thereby imaging a field-of-view including the open region and continuing in the body axis direction, an open region clearance and a field-of-view in the body axis direction can be enlarged without increasing the number of detectors.

The invention claimed is:

1. A PET scanner in which detector rings are arrayed in a multilayered manner so as to oppose each other in the body axis direction,
    wherein
    a predetermined number of detector units, each of which is made up of a predetermined number of detector rings, are arranged so as to give each other a clearance,
    a first ring set in which the clearance is less than or equal to a mean value of widths of two detector units forming each clearance and a second ring set constituted with a predetermined number of detector units, are arrayed apart so as to give a clearance which is less than or equal to a mean value of the width of the first ring set and that of the second ring set and is more than any clearance between the detector units constituting the first ring set, and
    a gantry is at least partially opened in accordance with at least some of the clearances between the detector units or between the ring sets,
    thereby imaging a field-of-view including the clearance and continuing in the body axis direction to an entire length of the first ring set and that of the second ring set.

2. The PET scanner according to claim 1, wherein a third ring set which internally houses at least the first ring set and the second ring set and a fourth ring set constituted with a predetermined number of detector units are arrayed apart so as to give a clearance which is less than or equal to a mean value of the width of the third ring set and that of the fourth ring set and is more than the clearances of the first ring set and the second ring set,
    thereby imaging a field-of-view including the clearance and continuing in the body axis direction to an entire length of the third ring set and that of the fourth ring set.

3. The PET scanner according to claim 1, wherein at least one of the detector units is a multiple ring-type detector.

4. The PET scanner according to claim 1, wherein a plurality of the same ring sets are included.

5. The PET scanner according to claim 1, wherein there are included a plurality of ring sets which are different at least in one of the number of detector units constituting the ring set, a width of the detector unit and a clearance between the detector units.

6. The PET scanner according to claim 1, wherein a dimension of the ring set in the body axis direction and/or an interval between the ring sets can be changed depending on the ring set and/or between the ring sets.

7. The PET scanner according to claim 1, wherein at least some of the detector units or the ring sets are structured so as to move in the body axis direction, thus making it possible to change at least some of the clearances.

8. The PET scanner according to claim 1, wherein a dimension of detecting element blocks constituting the detector unit in the body axis direction is equal to a dimension of the detector unit in the body axis direction.

9. The PET scanner according to claim 1, wherein a predetermined number of detecting element blocks arranged so as to give a clearance equal in dimension to an interval between the detector units are constituted in an integrated manner.

10. A method for deciding an arrangement of detectors which includes a step in which a detector ring constituted with detectors or detecting element blocks of width W is given as a unit [0], and units [0] in the number of D [0] are arranged apart to give an interval of $\alpha[0] \times W$, thereby giving an entire constitution of securing a field-of-view in the body axis direction continuing over all in width W [1], which is referred to as a unit [1], a step in which units [1] in the number of D[1] are arranged so as to give an interval of $\alpha[1] \times W[1]$, thereby giving an entire constitution of securing a field-of-view in the body axis direction continuing over all in width W [2], which is referred to as unit [2], and a step in which the above steps are repeated in the number of N to obtain a unit [N], in such a manner as to decide an arrangement of the detector rings in a PET scanner in which a plurality of detector units are arrayed so as to oppose each other, with a clearance kept in the body axis direction, thereby imaging a field-of-view including the clearance and continuing in the body axis direction.

* * * * *